United States Patent [19]

Abe

[11] Patent Number: 5,308,163
[45] Date of Patent: May 3, 1994

[54] CHECK VALVE FOR FLUID CONTAINERS AND A METHOD OF MANUFACTURING THE SAME

[75] Inventor: Tomematsu Abe, Numazu, Japan

[73] Assignee: Kabushiki Kaisha Nichiwa, Shizuoka, Japan

[21] Appl. No.: 33,273

[22] Filed: Mar. 16, 1993

[51] Int. Cl.⁵ .................... B65D 30/24; F16K 15/16
[52] U.S. Cl. ........................... 383/44; 137/846; 156/290; 251/149.1; 251/149.3
[58] Field of Search ............ 137/843, 846; 383/44, 383/56, 47; 156/290; 251/149, 149.1, 149.3

[56] References Cited

U.S. PATENT DOCUMENTS

| | | | |
|---|---|---|---|
| 2,584,632 | 2/1952 | Southwick | 156/290 |
| 3,282,412 | 11/1966 | Corella | 383/44 X |
| 3,313,472 | 4/1967 | Tjerneld | 383/44 |
| 3,430,842 | 3/1969 | Yamaguchi | 383/44 X |
| 5,144,708 | 9/1992 | Pekar | 137/846 X |

FOREIGN PATENT DOCUMENTS 1-78537 11/1987 Japan.
1-158442 4/1988 Japan.
2-79235 11/1988 Japan.

*Primary Examiner*—Robert G. Nilson
*Attorney, Agent, or Firm*—Flynn, Thiel, Boutell & Tanis

[57] ABSTRACT

A check valve comprises valve flaps formed by subjecting a front sheet and a rear sheet of synthetic resin, one of which is laid on top of the other, to heat sealing thereby sealing the same by thermal adhesion at the right and left sides thereof and at a plurality of curved heat sealings which are coupled to one another in such a way as to approximately form T-shapes at the junctions thereof so that the valve flaps have arabesque outlines. As a result, the lower parts of the heat sealings serve as fluid returning segments so as to improve the check valve in fluid sealing performance.

11 Claims, 1 Drawing Sheet

CHECK VALVE FOR FLUID CONTAINERS AND A METHOD OF MANUFACTURING THE SAME

BACKGROUND OF THE INVENTION

1. Field of the Invention

The present invention relates to a check valve for fluid containers, shock absorbing containers and so on (referred to fluid containers hereinafter), and more particularly to a check valve which is formed by subjecting opposing and walls of a flattened cylindrical body composed of a synthetic resin film or sheet to heat sealing to form a pair of heat sealed portions each comprising curved heat seals, the pair of heat sealed portions being arranged approximately symmetrically relative to a central axis of the flattened cylindrical body. The check valve prevents a fluid in a fluid container from leaking or flowing out of the containers and enables the fluid to be poured not only into the fluid container but also out of the container in a short time and with ease when the check valve is attached to a free side edge or opening of the fluid container. The fluid container is composed of a synthetic resin sheet or film which is made independently from the check valve. The container may contain a liquid and/or a gas.

2. Description of the Prior Art

Various check valves for synthetic resin film containers having a function of automatically closing a fluid inlet and outlet portion thereof have been proposed. These conventional check valves comprise a simple combination of linear heat sealed portions which form valve flaps therebetween and which are not provided with fluid returning segments. As a result, these check valves have a drawback of not being tight contact with each other this, fluid sealing performance is degraded. In addition, as the size of the valve flaps are increased, the less time is required to pour fluid into or out of the container, thus improving the efficiency of a fluid inlet and outlet passage of the check valve. However, as the size of the valve flaps increases, their sealing performance is remarkably lowered, which deteriorates the reliability and safety of the check valve. Moreover, when the sheet or film forming the fluid container is made of polyethylene etc. and the contained fluid is a gas such as air etc., the gas in the container is dispersed therefrom and the internal pressure of the container lowers due to the comparatively high permeability of the polyethylene etc. as time elapses, so that the sealing performance between the valve flaps deteriorates.

The leakage of fluid which has been poured into the container and contained therein is a serious phenomenon and is the major drawback of the prior art viewed in terms of reliability, safety, accuracy, etc. in the storage, transportation and supply thereof.

As mentioned above, the leakage of fluid which has been poured into and is contained in the container through the check valve is caused by the defective or deteriorated sealing performance of the valve flaps.

The foregoing deteriorated sealing performance of or between the valve flaps originates intrinsically from the process of heat sealing two or more thermoplastic resin films or sheets together to form a check valve. If the check valve is constructed simply of two opposing sheets of a rectangular film having two heat sealed edge portions extending longitudinally on opposite sides thereof, the valve flaps are deemed to be the sheets themselves. Each of the valve flaps (sheets) comprises a central portion and two peripheral portions each disposed between a heat sealed edge portion and a respective end of the central portion. The peripheral portions each terminate at coalescence points of both valve flaps (the point where the valve flaps and the respective heat sealed edge portion are joined).

It is generally believed that both valve flaps are forced into intimate and tight contact against each other over the full width thereof when pressed together by the internal pressure exerted by the fluid contained in the container. However, a close inspection of the two valve flaps shows the formation of fine or narrow gaps between the peripheral portions. The fluid contents in the container leaks out through the fine gaps in the peripheral portions while the central portions remain sealed due to the internal fluid pressure.

The reason for the formation of the fine gaps in the peripheral portions is considered to be the inhomogeneity of the valve flaps thus sealed under pressure. The central portion is uniform in every respect, but the peripheral portions are somewhat different from the central portion in some respects; viz. (1) a cantilever structure, (2) physical or mechanical properties especially as to behavior of elastic deformation due to thermal history induced by heat sealing and (3) elongation to some extent induced by the force of flowing fluid which has spread both flaps apart at the time of charging or discharging the container. In the case where linear seals are included in the check valve, in addition to heat sealing the edge portions, the linear seals are also heat sealed in order to define and to form them, therefore the conditions or circumstances mentioned above are similarly applicable.

Accordingly, if the check valve includes linear or polygonal heat sealed portions, the valve flaps are defined therebetween and comprise central portions which are separated from each other at maximum when the fluid is poured into or out of the container, and peripheral portions which are disposed on both sides of the central portions and which defined by and adjacent to the linear or polygonal heat sealed portions. Since the peripheral portions of the valve flaps are defined and formed by such a linear or polygonal lines, fine gaps are inevitably formed between the front and rear valve flaps at the peripheral portions, particularly at the corners where the polygonal lines make a turn. These fine gaps extending toward the outside make no more than a temporary resistance to the flow of the fluid thus making matters worse.

The fluid does not leak out through the central portion of the check valve where the valve flaps closely contact each other (due to fluid pressure) when the fluid is contained in the container. The fluid leaks out, however, as a result of a capillary action, i.e., a slit effect in the case of liquid, through the peripheral portions of the check valve which have the fine structural gaps therein, and as a result of a pressure gradient in the case of gas caused by the fact that the pressures in the gaps are higher than that outside the check valve (the atmosphere) though it is lower than that inside the check valve.

It is an object of the present invention to completely eliminate fluid leakage through a check valve.

SUMMARY OF THE INVENTION

The check valve for containers according to the present invention comprises valve flaps defined and formed by a pair of heat sealed portions each composed of a plurality of curved heat seals coupled to each other in such a way as to approximately form a T-shaped valve flap at the junction thereof which serves as a fluid returning segment. The T-shaped valve flaps are arranged approximately symmetrically relative to a central axis of the flattened check valve cylindrical body which provides valve flaps therebetween.

It is more effective to couple a third curved heat seal to a second curved heat seal to approximately form a second T-shape at the junction thereof in addition to coupling the second curved heat seal to a first curved heat sealing so as to approximately form a first T-shape at the junction thereof.

As described above, a plurality of curved heat sealed portions are coupled to one another in such a way as to approximately form T-shapes at the junctions thereof so that the lower parts of upper heat seals serve as fluid returning segments. Fluid which has entered a gap flows along an inner surface of a curved heat seal and is directed back by the fluid returning segment of the adjacent curved heat seal to form a stable low pressure chamber in a corner of the junction thereof as indicated by the dotted line in FIG. 1. Accordingly, the fluid flowing out of the fine gap, and subsequent supply thereof into the gap from the container is stopped so that the fluid in the container is completely prevented from leaking and discharging.

DESCRIPTION OF THE PREFERRED EMBODIMENT

An embodiment of the present invention will be described hereinafter with reference to the drawings.

Figure 3:
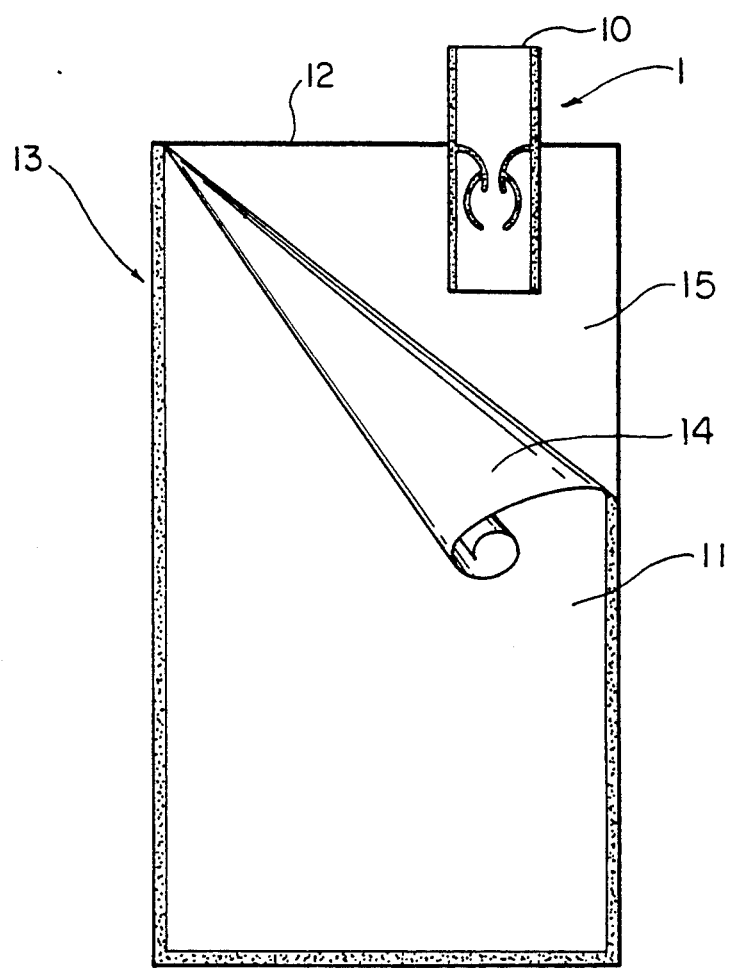
FIG. 3 is a partially cut away perspective view of a fluid container to which the check valve is attached.

With reference to FIG. 3, a fluid container 13 comprises a bag 11 and a check valve 1 partially disposed within, and projecting from the bag 11. Bag 11 comprises a flexible top sheet 14 aligned above or on top of a similarly sized flexible bottom sheet 15. Sheets 14 and 15 are heat sealed together by thermal adhesion at mutually opposing edges thereof along three of the four peripheral sides of bag 11. Bag 11 includes a free side or opening 12 which permits the check valve 1 to be interposed between sheets 14 and 15 prior to heat sealing the free side 12 to form the completely sealed fluid container 13 (notwithstanding the fluid inlet and outlet passage of the check valve discussed below).

Figure 1:
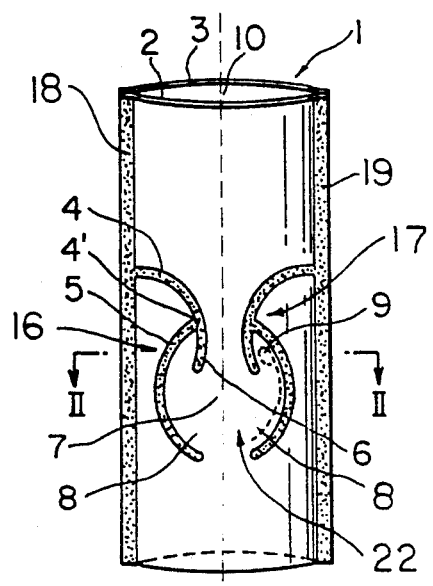
FIG. 1 is a perspective view of a check valve according to an embodiment of the present invention.
Figure 2:
FIG. 2 is a cross-sectional view of the check valve cut along the line II—II in FIG. 1.

As shown in FIG. 1, the check valve 1 includes a flexible top sheet 2 aligned above or on top of a similarly sized flexible bottom sheet 3. Sheets 2 and 3 are heat sealed together by thermal adhesion along mutually opposing edges thereof to form heat sealed edges or sides 18 and 19. The heat sealed edges 18 and 19 cooperate to define a fluid inlet and outlet passage or portion 10 therebetween which is adapted to receive a pouring spout (not shown) such as a nozzle or tap which charges and discharges fluid to and from the bag 11 via the inlet and outlet passage 10.

The check valve 1 also includes a pair of sidewardly spaced-apart heat sealed portions 16 and 17 arranged symmetrically relative to a central axis of the check valve 1. The heat sealed portions 16 and 17 cooperate to define valve flaps therebetween. Valve flap 22 (one shown) is the surface area of sheet 2 bounded on opposite sides by the heat sealed portions 16 and 17 (the second valve flap is a similarly bounded area of sheet 3). Each valve flap includes a central portion 7 disposed between the heat sealed portions and two peripheral portions 8 disposed on either side of the central portion 7. Each peripheral portion 8 in interposed between a respective end of the central portion and one of the heat sealed portions 16 and 17. The heat sealed portions 16 and 17 are similarly composed of a plurality of curved heat seals coupled to one another to approximately form T-shapes at the junctions thereof. The following description of heat sealed portion 16 is applicable in all respects to heat sealed portion 17. An upper curved heat seal 4 and a lower curved heat seal 5 are formed by heat sealing the sheets 2 and 3 together. Heat seal 4 is concave shaped with respect to the edge 18 while Heat seal 5 is convex with respect to the edge 19. The Lower heat seal 5 is coupled to an outwardly facing surface of the upper heat seal 4 to approximately form a T-shape at the junction 4' thereof. A lower portion of the upper heat seal 4 serves as a fluid returning segment or portion 6. The upper and lower heat seals 4 and 5 are subjected to the same capillary effect as conventional valve flaps i.e. in the case of liquid, it is the fluid that flows along the inner periphery of the heat seals 4 and 5 as a result of fine structural gaps between the peripheral portions 8 of the valve flaps, and in the case of gas, it is a result of a pressure gradient caused by the fact that the pressures in the gaps are higher than the pressure outside the check valve (atmospheric pressure) though lower the pressure inside the check valve.

In the case of fluid inside the container, the fluid which has flowed through the fine gap of the lower (second) heat seal 5 is turned back at the inside of the junction 4', and flows through the fine gap along the periphery of the fluid returning segment 6. The fluid enters a low pressure chamber or pocket 9 which is defined by the upper portion of the lower (second) heat seal 5 and the fluid returning segment 6. Fluid flow between the gaps of the peripheral portion along the lower heat seal 5 and the fluid return segment 6 is indicated by a dotted line in FIG. 1. The pressure in the low pressure chamber 9 increases to a certain extent as the fluid flows in until an equilibrium is reached. Such a slight incremental pressure increase in the low pressure chamber 9 is enough to prevent successive fluid from entering the chamber 9, thus stopping the capillary fluid flow from leaking out of the check valve 1.

The top sheets 14 and 2, and the bottom sheets 15 and 3 of the bag 11 and check valve 1, respectively, can be formed from a material selected from the group consisting of polyethylene and polypropylene.

The process for manufacturing the fluid container 13 of the present invention will now be described.

The check valve 1 according to the present invention is manufactured according to a process comprising the steps of first preparing the two sheets of polyethylene film 2 and 3 of 60 μm thick (40 mm in width and 120 mm in length) one of which is laid on top of the other. Second, the pair of curved heat sealed portions 16 and 17 (2 mm in width and 32 mm in length) are formed. Each heat sealed portion includes the a first curved heat seal 4 and the second curved heat seal 5 which are formed between the front sheet 2 and the rear sheet 3 and which are coupled to each other to approximately form a T-shape at the junction 4' thereof for providing the fluid returning segment 6 which is the lower part of the heat seal 4. Third, the left and right end edge portions of the sheets are subjected to a linear heat sealing. The first step can be replaced by flattening a cylindrical body of film or doubling a sheet of film of the same material. The heat sealing is performed by a heat sealer of an ordinary use at the temperature of 115° C. for 1 second. Each of the valve flaps, which is defined by the curved heat sealed portions 16 and 17 is composed of a valve flap central portion 7 and two valve flap peripheral portions 8, is 30 mm at the maximum width and 8 mm at the minimum width. The front sheet 2 and the rear sheet 3 form the fluid inlet and outlet portion 10 at the upper portions thereof for pouring fluid into or out of the container therethrough.

The bag 11 for holding a fluid or gas according to the present invention is manufactured according to the process comprising the steps of placing the first sheet 14 over the second sheet 15, both of polyethylene film of 100 μm thick and subjecting the same to heat sealing at the side edges thereof leaving one of the side edges as the opening 12. The fluid container 13 to which the check valve 1 of the present invention is attached is manufactured according to the process comprising the steps of inserting the check valve 1 into the opening 12 of the bag 11 and subjecting the whole opening 12 (excluding the fluid inlet and outlet portion 10 for pouring fluid into or out of the container) to heat sealing. The check valve 1 is inserted into the bag 11 through the opening 12 to the extent that the upper ends of the first curved heat seal 4 is not exposed above the opening 12. The externally projecting portion of the fluid inlet and outlet portion 10 forms the opening of the fluid container 13.

We poured oolong tea into the fluid container 13 through the fluid inlet and outlet portion 10 and placed the fluid container 13 on a table with the opening turned sideways. No oolong tea leaked out of the fluid container 13 after more than 168 hours elapsed. We made for comparison a fluid container which is the same as the fluid container 13 except that the heat sealing portions for defining and forming the valve flaps in the former were of a simple combination of linear heat seals (as in conventional check valves) and subjected it to the same leak test. Most of oolong tea leaked out and was lost after 8 hours elapsed.

The check valve according to the present invention seals up fluid for a long time to guarantee the safety and reliability of the fluid, can be easily attached to various fluid containers and also provides a better low-pollution and reusable shock absorbing or crating material compared with foamed polystyrene, etc. Particularly, the check valve can keep a sufficient fluid sealing performance even if the valve flaps are large, so that the check valve can have a large fluid inlet and outlet portion for rapid pouring of water, air, etc. into or out of the fluid container.

As the fluid container 13 thus manufactured has the check valve 1 being securely attached to the opening 12 of the bag 11 and having the fluid inlet and outlet portion 10 for the reception of a pouring spout such as nozzle and tap, charging thereof with the desired fluid is easily carried out. The fluid contained in the fluid container forces the valve flaps into close and tight contact against each other, while leaving the foregoing gaps filled with stagnant (not flowing) fluid, to produce a completely fluid-tight sealing.

Discharging of the fluid container 13 is also carried out easily using a rod or pipe (not shown). A rod or pipe is inserted into the fluid container through the externally projecting fluid inlet and outlet portion 10, and the tip thereof serves to spread apart the valve flaps as it advances, so that the fluid is ready for being drawn out by suction or gravity.

What is claimed is:

1. A process for manufacturing a check valve for fluid containers comprising the steps of:

aligning a first flexible sheet of film one of which is laid on top of a second flexible sheet of similarly sized film;

sealing said first and second sheets of film together by thermal adhesion to form first and second sidewardly spaced-apart heat sealed portions each including a first curved heat seal having first and second ends and a second curved heat seal joined to said first heat seal between said first and second ends to form a T-junction therebetween so that a pocket is defined between said second end of said first heat seal extending away from said T-junction and said second heat seal, said sheets of film as extending between said heat sealed portions defining valve flaps; and sealing said first and second sheets of film together by thermal adhesion to form first and second spaced-apart heat sealed edges extending adjacent to and respectively joined with said first ends of said heat sealed portions respectively to define a fluid inlet and outlet passage having said heat sealed portions disposed therein.

2. The process according to claim 1, wherein said sheets of film are formed of a synthetic resin.

3. The process according to claim 1, wherein said sheets of film are made from a material selected from the group consisting of polyethylene and polypropylene.

4. The process according to claim 1, wherein each of said valve flaps includes a central portion disposed between said heat sealed portions and peripheral portions interposed between said central portion and said respective heat sealed portion.

5. A check valve for a fluid container comprising:

first and second overlaying flexible sheets of film cooperating to define an elongate fluid inlet and outlet passage extending therebetween along a central axis;

said sheets of film having first and second spaced-apart heat sealed edges joined therebetween and extending substantially parallel with said central axis along opposite sides of said passage;

said sheets of film having first and second sidewardly spaced-apart heat sealed portions joined therebetween and arranged symmetrically within said passage relative to said central axis, said sheets of film as extending between said heat sealed portions defining valve flaps; and each of said heat sealed portions including a first curved heat seal having a first end joined with said respective heat sealed edge and a second free end disposed between said respective sealed edges and said central axis, a second curved heat seal joined to said first curved heat seal between said first and second ends to form a T-junction therebetween, and a fluid return pocket defined by said second end of said first curved heat seal extending away from said T-junction and said second seal.

6. The check valve according to claim 5, wherein said sheets of film are formed of a synthetic resin.

7. The check valve according to claim 5, wherein said sheets of film are made from a material selected from the group consisting of polyethylene and polypropylene.

8. The check valve according to claim 5, wherein each of said valve flaps further includes a valve flap central portion disposed between said heat sealed portions and valve flap peripheral portions interposed between said central portion and said respective heat sealed portion.

9. The check valve according to claim 5, wherein said first curved heat seals are concave with respect to said central axis, and said second curved heat seals are convex with respect to said central axis.

10. A container comprising:

first and second overlaying sheets of film cooperating to define a sealed bag having a plurality of heat sealed bag edges joined therebetween;

third and fourth overlaying sheets of film cooperating to define a check valve projecting from one of said plurality of heat sealed bag edges;

said check valve including a fluid inlet and outlet passage extending between said third and fourth sheets of film along a central axis and having an outer opening disposed at an end of said passage extending outside of said bag and an inner opening disposed at an end of said passage extending within said bag, first and second heat sealed check valve edges joined between said third and fourth sheets of film and extending substantially parallel to said central axis along opposite sides of said passage, first and second sidewardly spaced-apart heat sealed portions joined between said third and fourth sheets of film and arranged symmetrically within said passage relative to said central axis, and said third and fourth sheets of film as extending between said heat sealed portions defining valve flaps; and each of said heat sealed portions including a first curved heat seal having a first end joined with said respective check valve edge and a second free end projecting toward said inner opening and disposed between said respective check valve edge and said central axis, a second curved heat seal joined to said first heat seal between said first and second ends to form a T-junction therebetween and projecting toward said inner opening between said respective check valve edge and said central axis, and a fluid return pocket defined by said second free end extending from said T-junction and said second curved heat seal.

11. The container according to claim 10, wherein said first curved heat seals are concave with respect to said central axis, and said second curved heat seals are convex with respect to said central axis.

* * * * *